United States Patent [19]

Noel

[11] Patent Number: 5,141,964
[45] Date of Patent: Aug. 25, 1992

[54] COSMETIC COMPOSITIONS AND METHOD

[75] Inventor: Hugues Noel, Ermont, France

[73] Assignee: Roussel Uclaf, Paris, France

[21] Appl. No.: 570,225

[22] Filed: Aug. 21, 1990

[30] Foreign Application Priority Data

Aug. 23, 1989 [FR] France .................. 89-11170

[51] Int. Cl.⁵ ............ A61K 7/42; A61K 7/44; A61K 7/48; A61K 7/50
[52] U.S. Cl. ............ 514/777; 252/106; 424/59; 424/60; 514/781; 514/784; 514/788; 514/846; 514/847; 514/938; 514/944
[58] Field of Search ............ 514/847, 777, 844, 938; 252/106

[56] References Cited

U.S. PATENT DOCUMENTS

| | | | |
|---|---|---|---|
| 4,143,160 | 3/1979 | Osberghaus et al. | 514/784 |
| 4,146,649 | 3/1979 | Siegel et al. | 514/788 |
| 4,481,186 | 11/1984 | Deckner | 514/847 |
| 4,687,843 | 8/1987 | Smolin et al. | 514/847 |
| 4,818,751 | 4/1989 | Ibe | 514/847 |
| 4,835,665 | 5/1989 | Lang et al. | 514/847 |
| 4,851,434 | 7/1989 | Deckner | 514/847 |
| 4,973,473 | 11/1990 | Schneider et al. | 514/847 |

Primary Examiner—Dale R. Ore
Attorney, Agent, or Firm—Bierman and Muserlian

[57] ABSTRACT

A cosmetic composition comprising a cosmetic base containing an amount of a mixture of chitosan, glucosamine and at least one acid selected from the group consisting of succinic acid and gluconic acid sufficient to moisturize and improve the surface condition of the epidermis for treatment of the corium layer of the epidermis.

12 Claims, No Drawings

COSMETIC COMPOSITIONS AND METHOD

STATE OF THE ART

Numerous moisturizing products already exist. Products also exist which are intended for the conditioning of keratins, obtained for example by absorption of molecules containing one or more quaternary ammonium groups. But moisturizing of the corium layer by conventional moisturizers is accompanied by a decrease in the mechanical characteristics such as a decrease in elasticity or an increase in stretching ability. An increase in the transcutaneous permeability may also be observed.

OBJECTS OF THE INVENTION

It is an object of the invention to provide novel cosmetic compositions for moisturizing the skin while simultaneously improving the surface condition of the skin and to provide a novel method of moisturizing the skin.

These and other objects and advantages of the invention will become obvious from the following detailed description.

THE INVENTION

The novel cosmetic compositions of the invention are comprised of a cosmetic base containing an amount of a mixture of chitosan, glucosamine and at least one acid selected from the group consisting of succinic acid and gluconic acid sufficient to moisturize and improve the surface condition of the epidermis.

Chitosan or deacetylated chitosan can be obtained by hydrolyzing chitin which after cellulose, is the most common polysaccharide in nature. In the animal kingdom, chitin is an important structural element of the ligaments of certain invertebrates such as insects, molluscs, crustaceans and nematodes. In the vegetable kingdom, it is only found in the walls of mushrooms and certain Chlorophyceae algae. Bibliographical references on chitin and chitosan are Merck Index 10th Ed. No. 2017, "Chitin" Ed. MUZZARELLI R. A. A. Pergamon Press Oxford (1977) and "Chitine, chitosane et derives, de nouvelles prespectives pour l'industrie" SENG J. M. Biofutur (Vol. 9 1988) p. 40 to 44.

The combination of filmogenic and substantive (great affinity for skin, hair or nails) chitosan (chemically close to glycosaminoglycans of the dermis), of glucosamine and of an organic acid in a cosmetic product allows the rate at which the epidermis is moisturized to be increased and standard effects of often incompatible stretching agents (proteins of high molecular weight, anionic resins) and conditioners to be produced.

Preferably, the cosmetic compositions contain 0.2 to 5% by weight of chitosan, 0.2 to 5% by weight of glucosamine, 0.2 to 5% by weight of gluconic acid and/or 0.1 to 5% by weight of succinic acid, based on the weight of the final cosmetic compositions.

Preferably the chitosan includes 0 to 30% of acetylated amino groups or the chitosan comes from crab shells and includes less than 15% of acetylated amino groups and preferably 0.1 to 5%. The deacetylation rate of the chitin in chitosan should preferably be higher than 80% to allow total solubilization in a slightly acid medium.

Preferably, the cosmetic compositions contain one or more substances at a concentration sufficient to bring the pH of the preparation to between 3 and 6.5. Examples of suitable substances to be used to adjust the pH of the compositions are acetic acid, lactic acid, tartaric acid, malic acid, mucic acid, hydrobutyric acid, glycolic acid, hydroxycaproic acid, hydroxyoctanoic acid, aspartic acid, glutamic acid, pyrrolidone-carboxylic acid, hydrochloric acid and nitric acid Also useful are sodium, potassium and magnesium hydroxides, dimethylamino-ethanol, diethylaminoethanol, lysine, arginine, citrulline and ornithine.

The compositions of the invention are hygroscopic and their complete dehydration necessitates the use of a lyophilizing process. According to the composition of the mixture, the hygroscopicity is variable and allows the adaptation to different types of skin.

The process for the preparation of the compositions of the invention comprises first preparing an acid solution of a pH of less than 3.5 by mixing chitosan with at least one of gluconic and or succinic acid and then adding the other constituents of the composition.

The cosmetic compositions of the invention may also contain excipients adapted to all the forms used in cosmetology: creams or gels in pots or in tubes, milks, body emulsions, lotions in glass or plastic bottles and optionally in measuring bottles or also in jars, liquid soaps or dermatological bars.

For each form, appropriate excipients can be used which excipients must have all the qualities usually required. They must be endowed with a great affinity for the skin, be perfectly well tolerated, stable and present an adequate consistency allowing easy and agreeable use.

Examples of excipients which can be used are polymers of carboxyvinyl type, polyethyleneglycols, propyleneglycol, waxes, fatty substances, esters and triglycerides of fatty acids, stearic derivatives such as glycerol stearate, alcohols such as, for example, stearyl alcohols, cetostearyl alcohols, cetyl alcohol, polyol, polyoxyethylene cetyl ether, vegetable oils such as sweet almond oil, mineral oils such as vaseline oil, glycerine, lanolin derivatives, wetting agents, thickeners, stablizers, emulsifiers, preservatives, perfumes, colorants or other excipients known and currently used.

The cosmetic forms preferred are the cosmetic compositions as defined above, characterized in that they are presented in the form of creams, toners, emulsions for the body, liquid soaps or dermatological bars.

The method of the invention for moisturizing and improving the appearance of skin comprises applying an amount of a cosmetic composition of the invention in an amount sufficient to moisture and improve the appearance of skin.

In the following examples there are described several preferred embodiments to illustrate the invention. However, it should be understood that the invention is not intended to be limited to the specific embodiments. The hygroscopicity rate of the mixtures defined hereafter was determined.

EXAMPLE 1

| | |
|---|---|
| chitosan | 1 |
| gluconic acid | 0.5 |
| aspartic acid | 0.7 |
| glucosamine HCl | 0.5 |
| sodium hydroxide | 0.11 |
| absorption of water in an atmosphere of 80% relative humdity was 22%. | |

EXAMPLE 2

| | |
|---|---|
| chitosan | 1 |
| gluconic acid | 0.5 |
| glutamic acid | 0.8 |
| glucosamine HCl | 0.5 |
| L-arginine | 0.6 |
| absorption of water in an atmosphere of 80% relative humidity was 29.8%. | |

EXAMPLE 3

| | |
|---|---|
| chitosan | 1 |
| gluconic acid | 0.5 |
| pyrrolidonecarboxylic acid | 0.7 |
| glucosamine HCl | 0.5 |
| arginine | 0.6 |
| absorption of water in an atmosphere of 80% relative humidity was 31%. | |

EXAMPLE 4

| Moisturizing cream | |
|---|---|
| Water | 54 |
| Moisturizing mixture of Example 2 | 3.2 |
| Ethoxylated stearic acid 500 E | 2.5 |
| Ethoxylated stearic acid 100 E | 1.5 |
| Vegetable oil | 3 |
| Mineral oil | 15 |
| Phytosterol | 0.8 |
| Glycerol monostearate | 8 |
| Isopropyl myristate | 10 |
| Octyl methoxycinnamate | 2 |
| Preservative | s.q. |
| Perfume | s.q. |

EXAMPLE 5

| Sun moisturizing cream | |
|---|---|
| Octyl dimethylaminobenzoate | 5 |
| Cetyl alcohol | 5 |
| Sesame oil | 2 |
| Rice wax | 4 |
| Cetylstearyl ethylhexanoate | 3 |
| Cyclomethicone D5 | 7 |
| Ethoxylated cetyl alcohol 100 OE | 1 |
| Monaquat P TS ® (Mona) | 3.5 |
| Water | 66.2 |
| Perfume | s.q. |
| Preservative | s.q. |
| Moisturizing mixture of Example 3 | 3.3 |

EXAMPLE 6

| Moisturizing toner for greasy skin | |
|---|---|
| Water | 94.35 |
| Azulene | 0.1 |
| Nicotinamide | 0.2 |
| Moisturizing mixture of Example 1 | 4.05 |
| Ethoxylated octyldodecanol 30 OE | 1.3 |
| Perfume | s.q. |
| Preservative | s.q. |

EXAMPLE 7

| Body moisturizer | |
|---|---|
| Water | s.q. for 100 |
| Macadamia | 1.2 |
| Perhydrosqualene | 0.45 |
| Soja sterols | 0.3 |
| Linoleic acid | 0.15 |
| Glycerol monolinoleate | 0.30 |
| Glycerol undecylenate | 0.60 |
| Silicone oil | 2.00 |
| Hexyl decanol | 5.00 |
| Myristyl myristate | 5.00 |
| Propyleneglycol stearate | 1.50 |
| Glycerine | 3.00 |
| Carboxylic pyrrolic acid | 0.15 |
| Stearmidopropyl PG phosphate ammonium chloride | 3.00 |
| Preservatives | 2.00 |
| Mixture of Example 1 | 4.00 |
| Perfume | 0.30 |

EXAMPLE 8

| Bath oil | |
|---|---|
| Polyoxyethylene oleic alcohol | 9 |
| Polyoxyethylene lauric alcohol | 3 |
| Capric/caprylic acid glycerides P.O.E. | 8 |
| Macadamia oil | 1.2 |
| Perhydrosqualene | 0.45 |
| Soja sterols | 0.30 |
| Linoleic acid | 0.15 |
| Glycerol monolinoleate | 0.30 |
| Glycerol undecylenate | 0.60 |
| Polyethylene 400 | 10.00 |
| Dipropylene glycol | 21.00 |
| Water | s.q. for 100 |
| Lactamide MEA | 1.00 |
| Preservative | 0.05 |
| Anti-oxidant | 0.05 |
| Monoglyceride citrate | 0.1 |
| Mixture of Example 1 | 2.00 |
| Perfume | 0.50 |

EXAMPLE 9

| Cleansing gel | |
|---|---|
| Magnesium lauryl sulfate | 2.0 |
| 3-(3-cocoamidopropyl) dimethylammonium-2-hydroxypropane | 7.5 |
| Sodium cocoyl isothionate | 9.0 |
| Lauryl ether 2-amide MEA | 1.0 |
| Ethylene glycol monostearate | 2.0 |
| PEG-200 glyceryl monotalloate | 4.5 |
| Capric/caprylic acid glycerides P.O.E | 1.0 |
| Stearamidopropyl PG phosphate ammonium chloride | 2.0 |
| PEG-78 glyceryl mono cocoate | 0.5 |
| Water | q.s. for 100 |
| Preservatives | 2.0 |
| Perfume | 0.5 |
| Mixture of Example 2 | 4.0 |

Various modifications of the compositions and method of the invention may be made without departing from the spirit or scope thereof and it is to be understood that the invention is intended to be limited only as defined in the appended claims.

What I claim is:

1. A cosmetic composition comprising a cosmetically acceptable excipient containing an amount of a mixture of 0.2 to 5% by weight of chitosan, 0.2 to 5% by weight of glucosamine and at least one acid selected from the group consisting of 0.1 to 5% by weight of succinic acid and 1.2 to 5% by weight of gluconic acid sufficient to moisturize and improve the surface appearance of skin.

2. A composition of claim 1 wherein the chitosan contains 0 to 30% of acetylated amino group.

3. A composition of claim 1 wherein the chitosan is derived from crabshells and contains less than 15% acetylated amino groups.

4. A composition of claim 1 wherein the chitosan contains 0.1 to 5% of acetylated amino groups.

5. A composition of claim 1 wherein the pH is 3 to 6.5.

6. A composition of claim 1 in the form of a member selected from the group consisting of creams, toners, body emulsions, liquid soap and dermatological bars.

7. A method of moisturizing and improving the appearance of skin comprising applying an amount of a cosmetic composition of claim 1 sufficient to moisture and improve the appearance of skin.

8. A method of claim 7 wherein the chitosan contains 0 to 30% of acetylated amino groups.

9. A method of claim 7 wherein the chitosan is derived from crabshells and contains less than 15% acetylated amino groups.

10. A method of claim 7 wherein the chitosan contains 0.1 to 5% of acetylated amino groups.

11. A method of claim 8 wherein the pH is 3 to 6.5.

12. A method of claim 7 wherein the mixture is in the form of a member selected from the group consisting of creams, toners, body emulsions, liquid soap and dermatological bars.

* * * * *